United States Patent
Zamarripa et al.

(10) Patent No.: US 10,729,508 B2
(45) Date of Patent: Aug. 4, 2020

(54) MULTI-CHAMBERED BREAST TISSUE EXPANDER

(71) Applicant: Medtronic Advanced Energy, LLC, Minneapolis, MN (US)

(72) Inventors: Nathan Zamarripa, Kittery Point, MN (US); Mark Guirguis, Boston, MA (US); Nicholas Valley, Portsmouth, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 370 days.

(21) Appl. No.: 15/903,229

(22) Filed: Feb. 23, 2018

(65) Prior Publication Data

US 2018/0256276 A1   Sep. 13, 2018

Related U.S. Application Data

(60) Provisional application No. 62/467,989, filed on Mar. 7, 2017.

(51) Int. Cl.
  *A61B 90/00*   (2016.01)
  *A61F 2/12*    (2006.01)
  *A61B 17/00*   (2006.01)

(52) U.S. Cl.
  CPC ............ *A61B 90/02* (2016.02); *A61F 2/12* (2013.01); *A61B 2017/00212* (2013.01); *A61B 2017/00221* (2013.01); *A61B 2017/00557* (2013.01); *A61F 2250/0001* (2013.01); *A61F 2250/0003* (2013.01); *A61F 2250/0004* (2013.01); *A61F 2250/0048* (2013.01)

(58) Field of Classification Search
  CPC ............... A61F 2/12; A61F 2250/0003; A61F 2250/0004; A61F 2250/0048; A61F 5/0003; A61F 5/0013; A61F 5/003; A61F 5/0033; A61F 5/0036; A61F 5/004; A61F 5/0046; A61B 90/02
  See application file for complete search history.

(56) References Cited

U.S. PATENT DOCUMENTS

| | | | |
|---|---|---|---|
| 7,951,111 B2 | 5/2011 | Drasler et al. | |
| 8,758,386 B2 | 6/2014 | Gelbart | |
| 8,979,886 B2 | 3/2015 | Campbell et al. | |
| 9,504,807 B2 | 11/2016 | Drasler et al. | |
| 9,526,584 B2 | 12/2016 | Payne et al. | |
| 2006/0069403 A1 | 3/2006 | Shalon et al. | |
| 2007/0233273 A1* | 10/2007 | Connell | A61F 2/12 623/23.72 |
| 2008/0021546 A1 | 1/2008 | Patz et al. | |
| 2009/0264820 A1 | 10/2009 | Kung | |
| 2011/0153017 A1* | 6/2011 | McClellan | A61B 90/02 623/8 |
| 2014/0236210 A1* | 8/2014 | Payne | A61F 2/12 606/192 |

* cited by examiner

*Primary Examiner* — Darwin P Erezo
*Assistant Examiner* — Christian D Knauss
(74) *Attorney, Agent, or Firm* — Christopher & Weisberg, P.A.

(57) ABSTRACT

A tissue expansion device with a plurality of lobes made from non-compliant material, each lobe defining a chamber therein. Each chamber is fluidly isolated from every other chamber in the plurality of lobes. Each chamber has an inflation element with a valve to release a pressurized fluid to inflate the lobe to expand a cavity, and a deflation element with a valve to deflate the lobe by compressing the fluid.

20 Claims, 3 Drawing Sheets

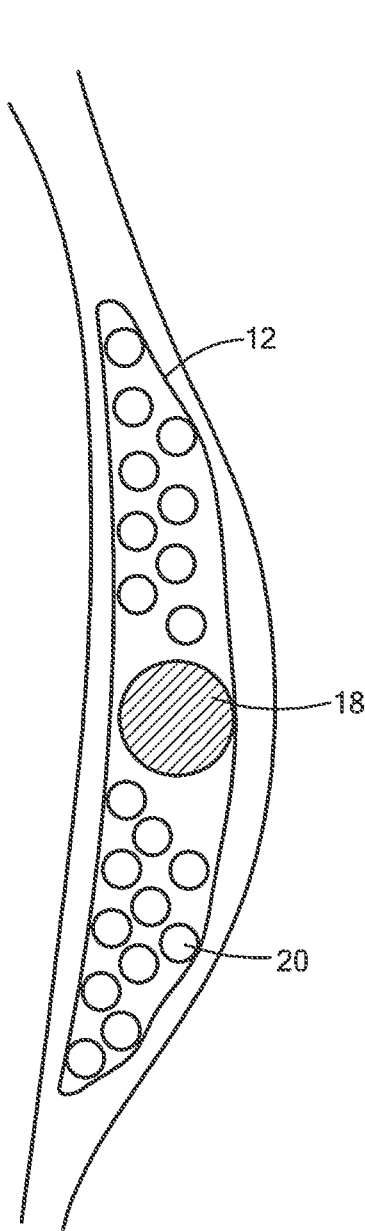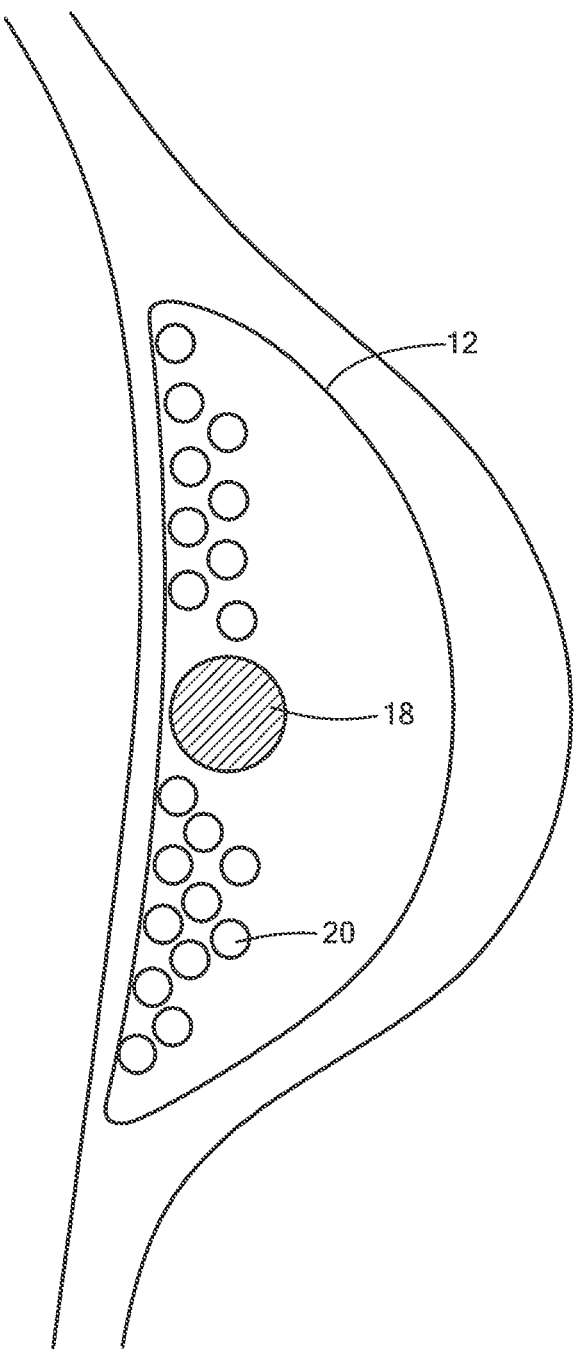
*FIG. 3A*  *FIG. 3B*

MULTI-CHAMBERED BREAST TISSUE EXPANDER

PRIORITY CLAIM

This application claims the benefit of the filing date of provisional U.S. patent application Ser. No. 62/467,989, filed 7 Mar. 2017.

TECHNICAL FIELD

This disclosure relates to a method and apparatus for expanding a cavity in human tissue.

BACKGROUND

A common breast reconstruction technique is tissue expansion, which involves expansion of the breast skin and muscle using a temporary tissue expander. Currently available tissue expanders are generically sized (small, medium, and large) and create a single breast mount geometry. However, owing to the limited number of sizes of such expanders, the size of the expanded pocket is limited to the preset number of sizes available for the tissue expanders. Moreover, it is not uncommon for tissue expanders to experience unwanted migration of the laterally or inferiorly.

Other tissue expanders, such as coronary balloons, are small in diameter and have cylindrical geometries, while breast air expanders are large diameter and generally spherical in geometries. The pressure required to inflate a balloon is inversely proportional to the diameter of the balloon. Therefore, the pressure requirements to expand a blood vessel versus muscle and skin are significantly different. Moreover, the anatomies being mechanically altered by the balloon/expander are different; coronary balloons are designed to alter plaque inside the vascular system. Conversely, breast air expanders are intended to move chest wall muscle, tendon and skin, which has entirely different properties than plaque or blood vessels. Thus, coronary balloons are not suitable as breast tissue expanders.

SUMMARY

Some embodiments advantageously provide a tissue expansion device include a plurality of lobes, each of the plurality of lobes being molded to at least one other of the plurality of lobes and be composed of a non-compliant material. Each of the plurality of lobes defines a chamber therein, each chamber is fluidly isolated from every other chamber in the plurality of lobes. Each chamber includes at least one positively pressurized inflation element configured to inflate the corresponding lobe, the at least one inflation element including a first valve configured to release pressurized fluid from within the at least one inflation element, the corresponding lobe being configured to expand a cavity within breast tissue of a patient when the corresponding lobe is inflated. Each chamber includes a plurality of negatively pressurized deflation elements configured to deflate the corresponding lobe, the plurality of deflation elements including a second valve configured to open the plurality of deflation elements to receive, retain, and compress fluid from the corresponding lobe.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein:

FIG. 3A is a side cross-sectional view of one of the lobes of the device in a deflated state; and FIG. 3B is a side cross-section view of the device shown in FIG. 3A in an inflated state.

DETAILED DESCRIPTION

As used herein, relational terms, such as "first" and "second," "top" and "bottom," and the like, may be used solely to distinguish one entity or element from another entity or element without necessarily requiring or implying any physical or logical relationship or order between such entities or elements.

Figure 1:
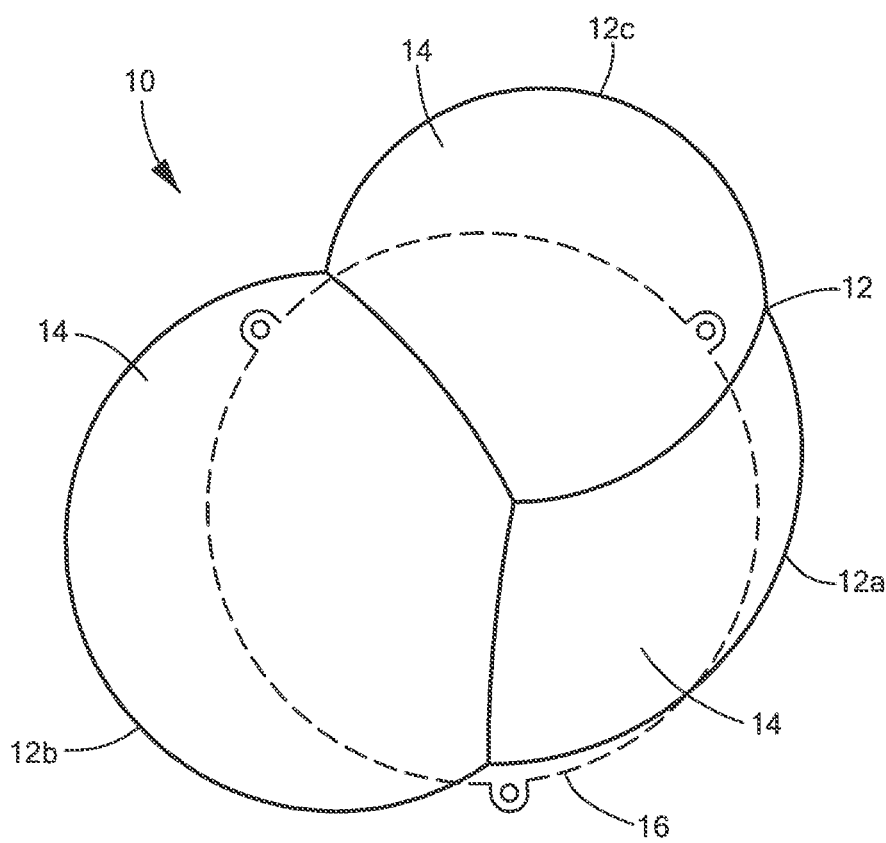
FIG. 1 is a front view of a tissue expansion device constructed in accordance with the principles of the present application.

Now referring to the drawings in which like reference designators refer to like elements, there is shown in FIG. 1 an exemplary tissue expansion device constructed in accordance with the principles of the present application and designated generally as "10," The device 10 includes a plurality of expansion lobes 12 coupled together and fluidly isolated from one another. In an exemplary configuration, the plurality of expansion lobes 12 includes three lobes, namely, lobe 12a, 12b, and 12c (collectively referred to as lobes 12), and in other configurations any number of lobes 12 may be included. Each lobe 12 defines a chamber 14 therein configured to retain a volume of fluid. In one configuration, each lobe 12 is configured to retain a volume of liquid, such as water or saline, or gas such as air, helium, argon, carbon dioxide, or other inert gases. It is contemplated that both compressible and incompressible fluids may be retained within each chamber 14 and each chamber 14 may include the same or different fluid.

The lobes 12 may be composed of a non-compliant inflatable member, for example, a non-compliant balloon. The non-compliant nature of each lobe 12 described herein means that each lobe 12 may expand approximately 5-10% when inflated versus compliant balloons which can expand between 100-600%. Non-compliant materials that may comprise each lobe 12 may include, but are not limited to, PET, PET/Urethane, Polyurethanes, PVC, cross-linked polyethylene, polyolefins, nylon, and nylon elastomer. In an exemplary configuration, each lobe 12 is a non-compliant balloon composed of PET having a wall thickness in the range 5-50 microns and is molded to at least one other lobe 12 in the plurality of lobes 12. In such a configuration, when the lobes 12 are inflated, the patient's anatomy conforms to the lobes 12. In one configuration, lobe 12a is configured to expand medially; lobe 12b is configured to expand laterally, and lobe 12c is configured to expand superiorly. In other configurations, the device 10 may include a fourth lobe 12 (not shown) configured to expand inferiorly. The diameters of each lobe 12 of the plurality of lobes 12 may be the same or different and the device 10 is sized to be inserted without any percutaneous connections. For example, the device 10 may be inserted within a cavity within breast tissue and is configured to expand skin, muscle, fascia, and/or tendon. In other configuration, the device 10 may be inserted within any cavity within the body.

Continuing to refer to FIG. 1, the device 10 may be mounted within the breast cavity of the patient, for example, a cavity created following a mastectomy, with mounting element 16. The mounting element 16 may include a ring or other base configured to be attached to tissue on one end and to the device 10 on another end. For example, the mounting element 16 may include attachment points, for example, loops that facilitate the suturing of the mounting element 16 to the target tissue region, fix example, with a surgical stapler to the chest ostium. In one configuration of the device having three lobes 12, three attachment points are included. The device 10 may be molded or otherwise affixed to the opposite end of the mounting element 16. When the device 10 is removed, the sutures may be cut and the device 10 may be pulled out from the pocket that is created. The affixation of the device 10 to mounting element 16 and attachment of mounting element 16 to tissue prevent unwanted migration of the device 10.

Figure 2:
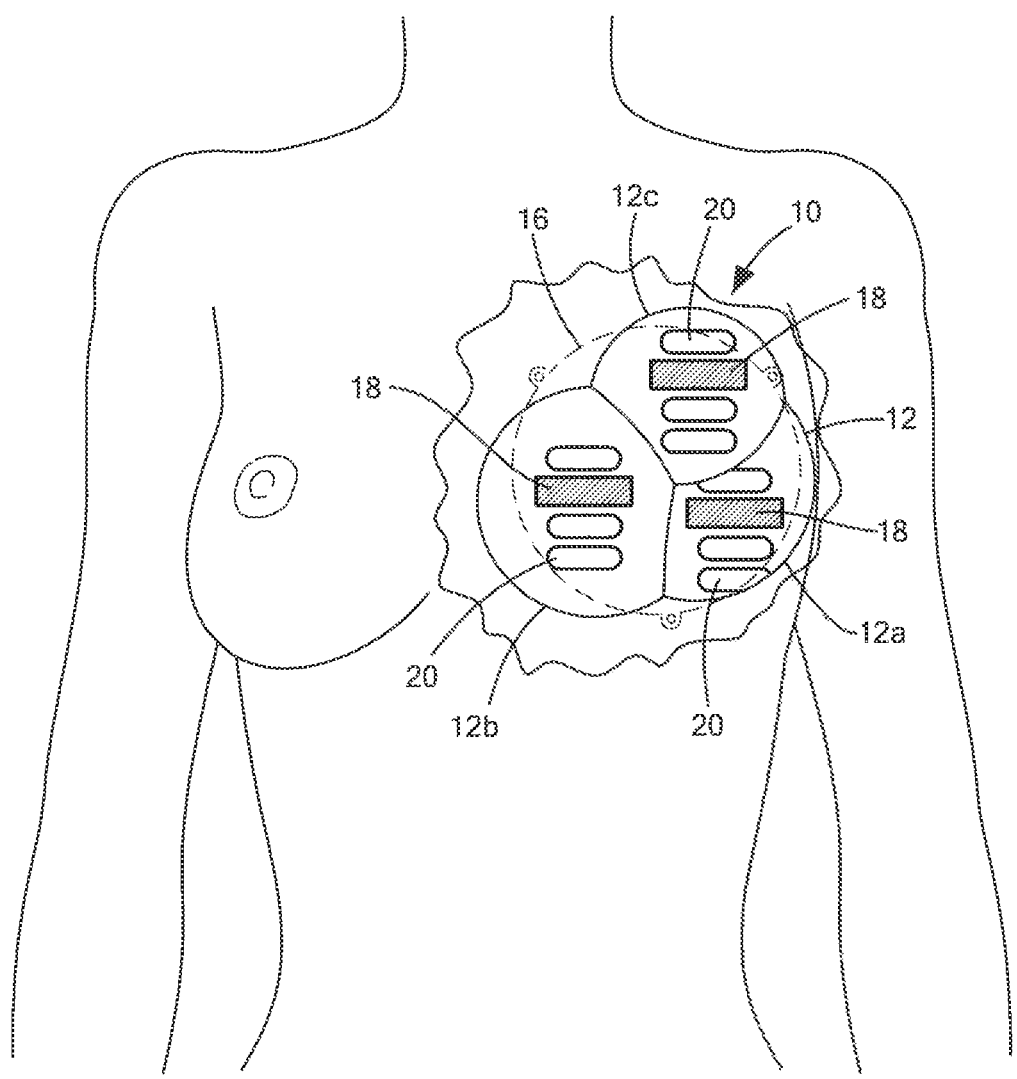
FIG. 2 is a front inside view of the device shown in FIG. 1 inserted within the breast of a patient.

Referring now to FIGS. 2-3B, each lobe 12 includes at least one inflation element 18 and at least one deflation element 20 to independently control the inflation/deflation of each lobe 12. For example, the inflation element 18 may be a rigid cylinder coupled to the interior of each respective chamber 14. Each inflation element 18 may include a valve configured to release a positively pressurized fluid, for example, compressed $CO_2$, air, or an inert gas. The valve may be those known in the art, for example, electro-mechanical valve such a solenoid valve that may be activated wirelessly. For example, a remote device accessible by the user and/or doctor may include a wireless transmitter in communication with a wireless receiver in the inflation element 18. The wireless transmitter may send a signal configured to activate the electro-mechanical valve and release the pressurized fluid, either all at once as a bolus, or in the form of a controlled incremental release. For example, a control panel on the remote device may include a first actuator configured to release all the air from the inflation element 18, or may include, for example, a first actuator configured to release a predetermined amount of pressurized fluid from one of the plurality of lobes 12 or all of the plurality of lobes 12 simultaneously. That is, the user and/or doctor may actuate the remote device to independently and controllably release a predetermined amount of compressed fluid in each or all the lobes 12.

Continuing to refer to FIGS. 2-3B, a plurality of negatively pressurized deflation elements 20 may be affixed within each lobe 12 to deflate their respective lobe 12. The plurality of deflation elements 20 may be of similar construction to the inflation elements 18 in that they may include a rigid canister and a valve, for example, an electro-mechanical valve that opens each deflation element 20 to the volume of fluid within each lobe 12. The plurality of deflation elements 20, however, may be smaller in size that the inflation elements 18 and may be more numerous. A second actuator may be included as part of the remote device to communicate with the plurality of deflation elements 20. For example, all of the deflation elements 20 in all of the lobes 12 may be configured to deflate the device for removal, either all at once or incrementally. Alternatively, each of the deflation elements 20 may be activated in each corresponding lobes 12 independently of deflation elements 20 in other lobes. For example, all of the deflation elements 20 may be simultaneously activated in, for example, lobes 12*a* and not in lobes 12*b* and 12*c*. As with the inflation element 18, the deflation elements 20 may include a wireless transmitter/receiver such that they may be actuate wirelessly be the remote device through the skin and tissue of the patient.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings without departing from the scope of the following embodiments.

The invention claimed is:

1. A tissue expansion device, comprising:
 a plurality of lobes, each of the plurality of lobes being molded to at least one other of the plurality of lobes and comprising a non-compliant material;
 each of the plurality of lobes defining a chamber therein, each chamber being fluidly isolated from every other chamber in the plurality of lobes;
 each chamber including at least one positively pressurized inflation element disposed therein that is configured to inflate a corresponding lobe, the at least one positively pressurized inflation element including a first valve configured to release pressurized fluid from within the at least one positively pressurized inflation element,
 the corresponding lobe being configured to expand a cavity within breast tissue of a patient when the corresponding lobe is inflated; and
 each chamber including a plurality of negatively pressurized deflation elements disposed therein that are configured to deflate the corresponding lobe, the plurality of negatively pressurized deflation elements including a second valve configured to open the plurality of negatively pressurized deflation elements to receive, retain, and compress fluid from the corresponding lobe.

2. The device of claim 1, wherein the plurality of lobes includes three lobes, and wherein when the three lobes are implanted within breast tissue a first of the three lobes is configured to inflate superiorly, a second of the three lobes is configured to inflate laterally, and a third of the three lobes is configured to inflate medially.

3. The device of claim 2, wherein the non-complaint material is PET.

4. The device of claim 1, wherein the non-complaint material is PET.

5. The device of claim 1, wherein each of the plurality of lobes is independently inflatable.

6. The device of claim 5, wherein each of the plurality of lobes is independently deflatable.

7. The device of claim 6, wherein the first valve and the second valve are wirelessly controllable.

8. The device of claim 1, wherein when the device is implanted within a breast, the device has no percutaneous connections.

9. The device of claim 1, wherein the first valve is controllable to release a predetermined amount of pressurized fluid.

10. The device of claim 1, wherein the pressurized fluid is carbon dioxide.

11. The device of claim 1, wherein the pressurized fluid in an inert gas.

12. The device of claim 1, further comprising a mounting element, wherein the plurality of lobes are affixed to the mounting element.

13. The device of claim 12, wherein the mounting element is configured to be sutured within a breast.

14. A tissue expansion device, comprising:
 a mounting element; and a plurality of lobes, each of the plurality of lobes being molded to at least one other of the plurality of lobes and comprising a non-compliant material;

each of the plurality of lobes defining a chamber therein, each chamber being fluidly isolated from every other chamber in the plurality of lobes;

each chamber including at least one positively pressurized inflation element disposed therein that is configured to inflate a corresponding lobe, the at least one positively pressurized inflation element including a first valve configured to release pressurized fluid from within the at least one positively pressurized inflation element, the corresponding lobe being configured to expand a cavity within breast tissue of a patient when the corresponding lobe is inflated; and each chamber including a plurality of negatively pressurized deflation elements disposed therein that are configured to deflate the corresponding lobe, the plurality of negatively pressurized deflation elements including a second valve configured to open the plurality of negatively pressurized deflation elements to receive, retain, and compress fluid from the corresponding lobe;

wherein the plurality of lobes includes at least three lobes, and wherein when the lobes are implanted within breast tissue, a first of the at least three lobes is configured to inflate superiorly, a second of the at least three lobes is configured to inflate laterally, and a third of the at least three lobes is configured to inflate medially;

wherein each of the plurality of lobes is independently inflatable and deflatable; and wherein the plurality of lobes are affixed to the mounting element.

15. The device of claim 14, wherein the non-complaint material is PET.

16. The device of claim 14, wherein when the device is implanted within a breast, the device has no percutaneous connections.

17. The device of claim 14, wherein the first valve and second valve are wirelessly controllable.

18. The device of claim 17, wherein the first valve is controllable to release a predetermined amount of inert gas.

19. The device of claim 14, wherein the mounting element is configured to be sutured within a breast.

20. A tissue expansion device, comprising:

a mounting element, wherein the mounting element is configured to be sutured within the breast; and three lobes, each of the lobes being molded to at least one other lobes and comprising PET;

each of the lobes defining a chamber therein, each chamber being fluidly isolated from every other chamber in the plurality of lobes;

each chamber including at least one positively pressurized inflation element disposed therein that is configured to inflate a corresponding lobe, the at least one positively pressurized inflation element including a first valve configured to release pressurized fluid from within the at least one positively pressurized inflation element, the corresponding lobe being configured to expand a cavity within breast tissue of a patient when the corresponding lobe is inflated;

each chamber including a plurality of negatively pressurized deflation elements disposed therein that are configured to deflate the corresponding lobe, the plurality of negatively pressurized deflation elements including a second valve configured to open the plurality of negatively pressurized deflation elements to receive, retain, and compress fluid from the corresponding lobe;

wherein when the three lobes are implanted within breast tissue, a first of the three lobes is configured to inflate superiorly, a second of the three lobes is configured to inflate laterally, and a third of the three lobes is configured to inflate medially;

wherein each of the lobes is independently inflatable and deflatable;

wherein each of the lobes is affixed to the mounting element;

wherein the first valve is controllable to release a predetermined amount of inert gas;

and wherein the first valve and the second valve are wirelessly controllable.

* * * * *